United States Patent [19]

King

[11] Patent Number: 5,120,697
[45] Date of Patent: * Jun. 9, 1992

[54] ALKOXYLATION USING MODIFIED CALCIUM-CONTAINING CATALYSTS

[75] Inventor: Stephen W. King, Scott Depot, W. Va.

[73] Assignee: Union Carbide Chemicals & Plastics Technology Corporation, Danbury, Conn.

[*] Notice: The portion of the term of this patent subsequent to May 19, 2009 has been disclaimed.

[21] Appl. No.: 251,434

[22] Filed: Sep. 30, 1988

[51] Int. Cl.⁵ .................................................. B01J 31/00
[52] U.S. Cl. ................................... 502/162; 502/167; 502/168; 502/170; 502/171; 502/172
[58] Field of Search ............... 502/162, 167, 168, 170, 502/171, 172

[56] References Cited

U.S. PATENT DOCUMENTS

| | | | |
|---|---|---|---|
| 2,934,505 | 4/1960 | Gurgiolo | 260/2 |
| 3,328,306 | 6/1967 | Ellis | 252/90 |
| 3,432,445 | 3/1969 | Oagan et al. | 260/2 |
| 3,607,785 | 9/1971 | Oagan et al. | 252/431 C |
| 3,682,849 | 8/1972 | Smith et al. | 260/615 B |
| 4,098,818 | 7/1978 | Krummel et al. | 260/535 R |
| 4,112,231 | 9/1978 | Weibull et al. | 544/174 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,281,087 | 7/1981 | Heuschen et al. | 525/361 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,326,047 | 4/1982 | Yates | 525/507 |
| 4,359,589 | 11/1982 | Brownscombe | 568/618 |
| 4,360,698 | 11/1982 | Sedan | 568/618 |
| 4,375,564 | 3/1983 | Edwards | 568/618 |
| 4,396,779 | 8/1983 | Edwards | 568/618 |
| 4,396,780 | 8/1983 | Shtykh et al. | 568/620 |
| 4,430,252 | 2/1984 | Ryu | 502/171 |
| 4,453,022 | 6/1984 | McCain et al. | 568/618 |
| 4,453,023 | 6/1984 | McCain et al. | 568/618 |
| 4,456,691 | 6/1984 | Yang | 502/171 |
| 4,465,877 | 8/1984 | Edwards | 568/618 |
| 4,472,560 | 9/1984 | Kuyper et al. | 526/120 |
| 4,474,678 | 10/1984 | Lutz et al. | 252/174.21 |
| 4,477,589 | 10/1984 | van der Hulst et al. | 502/169 |
| 4,483,941 | 11/1984 | Yang | 502/171 |
| 4,490,561 | 12/1984 | Yang et al. | 568/615 |
| 4,568,774 | 2/1986 | Yang | 568/616 |
| 4,654,417 | 3/1987 | Inoue et al. | 528/416 |
| 4,659,778 | 4/1987 | Williams | 525/107 |
| 4,665,236 | 5/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |
| 4,754,075 | 6/1988 | Knopf et al. | 568/618 |
| 4,775,653 | 10/1988 | Leach et al. | 502/170 |
| 4,892,977 | 1/1990 | Nieh | 568/618 |

FOREIGN PATENT DOCUMENTS

| | | |
|---|---|---|
| 0026544 | 4/1981 | European Pat. Off. |
| 0026546 | 4/1981 | European Pat. Off. |
| 0026547 | 4/1981 | European Pat. Off. |
| 0033359 | 6/1981 | European Pat. Off. |
| 0046582 | 3/1982 | European Pat. Off. |
| 0082569 | 6/1983 | European Pat. Off. |
| 0085167 | 6/1983 | European Pat. Off. |
| 0092256 | 10/1983 | European Pat. Off. |
| 0095562 | 12/1983 | European Pat. Off. |
| 0104309 | 4/1984 | European Pat. Off. |
| 0133715 | 3/1985 | European Pat. Off. |
| 0180266 | 5/1986 | European Pat. Off. |
| 0180267 | 5/1986 | European Pat. Off. |
| 0212820 | 3/1987 | European Pat. Off. |
| 0289159 | 11/1988 | European Pat. Off. |
| 1462133 | 1/1977 | United Kingdom |
| 1462134 | 1/1977 | United Kingdom |
| 1399966 | 7/1985 | United Kingdom |

OTHER PUBLICATIONS

Kochurovskaya, G. G. et al., Kriobiol. Kriomed., 3, 1977, pp. 76-79.

Turova, N. Y. et al., Chemical Reviews-Uspekhi Khimii, Mar. 1965, pp. 161-185.

U.S. Patent Application Serial No. 186,937, filed Apr. 27, 1988 (D-12555-1).

U.S. Patent Application Serial No. 186,938, filed Apr. 27, 1988 (D-12337).

Schick, M. J., Nonionic Surfactants, vol. 1, Marcel Dekker, Inc., New York, N.Y. (1967), pp. 28-41.

U.S. patent application Ser. No. 454,560, filed Dec. 30, 1982 (D-13322).

U.S. patent application Ser. No. 102,939, filed Sep. 30, 1987, (D-15778).

Primary Examiner—Patrick P. Garvin
Assistant Examiner—E. D. Irzinski
Attorney, Agent, or Firm—Rose M. Allen

[57] ABSTRACT

This invention relates to modified calcium-containng catalysts and the use thereof in the preparation of alkoxylation products, i.e., condensation reaction products of alkylene oxides and organic compounds having at least one active hydrogen. In another aspect of this invention, processes are provided for preparing modified calcium-containing catalysts for alkoxylation using calcium metal or a calcium-containing compound, e.g., calcium oxide or calcium hydroxide, as sources for the catalytically-active calcium and at least one divalent or polyvalent metal salt of an oxyacid as a modifier. In a further aspect of this invention, processes are provided for preparing alkoxylaton products that have beneficial, narrow molecular weight ranges using the modified calcium-containing catalysts.

22 Claims, No Drawings

ALKOXYLATION USING MODIFIED CALCIUM-CONTAINING CATALYSTS

RELATED APPLICATIONS

The following are related, commonly assigned applications, filed on an even date herewith:
U.S Patent Application Ser. No. 251,430, now U.S. Pat. No. 4,946,984; U.S. Patent Application Ser. No. 251,433; U.S. Patent Application Ser. No. 251,432; U.S. Patent Application Ser. No. 251,436; and U.S. Patent Application Serial No. 251,431.

BRIEF SUMMARY OF THE INVENTION

Technical Field

This invention relates to modified calcium-containing catalysts and the use thereof in the preparation of alkoxylation products, i.e., condensation reaction products of alkylene oxides and organic compounds having at least one active hydrogen. In another aspect of the invention, processes are provided for preparing modified calcium-containing catalysts for alkoxylation using calcium metal or a calcium-containing compound, e.g., calcium oxide or calcium hydroxide, as sources for the catalytically-active calcium and at least one divalent or polyvalent metal salt of an oxyacide as a modifier. In a further aspect of the invention, processes are provided for preparing alkoxylation products that have beneficial, narrow molecular weight ranges using the modified calcium-containing catalysts.

BACKGROUND OF THE INVENTION

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a greater portion of water is usually required otherwise gelling (evidencing product instability) may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
| --- | --- | --- |
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % |  |  |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, Published Dec. 12, 1983, exemplifies the ability to obtain high selectivity to low ethoxylate species when low ratios of ethylene oxide reactant to alcohol are employed as well as the tendency to rapidly lose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
| --- | --- | --- |
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Recently, Yang and coworkers were granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093. Significantly, these patents contain statements to the effect that the oxides and/or hydroxides of magnesium and calcium do not exhibit catalytic activity for ethoxylation, although they may function in the role of promoters for the barium and strontium compounds (U.S. Pat. No. 4,302,613).

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most Prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European patent publication No. 0026544, No. 0026547, and No. 0026546, all herein incorporated by reference. These workers have also disclosed the use of strong acids to partially neutralize and thereby promote the catalytic action of certain alkaline earth metal derivatives. See U.S. Pat. No. 4,453,022 and U.S. Pat. No. 4,453,023 (barium-containing catalyst), both herein incorporated by reference. These workers also tend to confirm Yang's findings as to calcium oxide, in that McCain et al. teach that calcium oxide does not form a lower alkoxide when treated with ethanol.

In particular, calcium metal or calcium hydride is typically the starting material used by McCain et al. to make the calcium-containing catalyst. These starting materials, however, are expensive. Consequently, a desire exists to use commonly found sources of calcium, such as calcium oxide (quicklime) and calcium hydroxide (slaked lime), to make calcium-containing catalysts for alkoxylation. Moreover, quicklime and slaked lime are by far the cheapest, most plentiful, least noxious, and most environmentally-acceptable of all the alkaline earth metal derivatives.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

U.S. Pat. Nos. 4,754,075, 4,886,075, 4,886,917 and 4,820,673, herein incorporated by reference, relates to processes for preparing alkoxylation mixtures having relatively narrow alkoxylation product distributions using modified, calcium-containing catalysts. Processes are also disclosed for making alkoxylation catalysts using calcium oxide and/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

U.S. Pat. No. 4,902,658, herein incorporated by reference, relates to heterogeneous (organic polymer-supported) calcium-containing catalysts and the use thereof in the preparation of alkoxylation products, i.e., condensation reaction products of alkylene oxides and organic compounds having at least one active hydrogen. Processes are provided for preparing heterogeneous (organic polymer-supported) calcium-containing catalysts for alkoxylation using calcium oxide or calcium hydroxide as sources for the catalytically-active calcium. Alkoxylation products are provided that have beneficial, narrow molecular weight ranges and are essentially neutral in pH and free from catalyst residues.

Disclosure of the Invention

This invention relates to modified calcium-containing alkoxylation catalysts and to processes for making the catalysts using calcium metal or a calcium-containing compound, e.g., calcium oxide or calcium hydroxide, as sources for the catalytically-active calcium and at least one divalent or polyvalent metal salt of an organic or inorganic oxyacide as a modifier. This invention further relates to processes for preparing alkoxylation product mixtures having relatively narrow alkoxylation product distributions using the modified calcium-containing catalysts.

The modified calcium-containing catalysts of this invention are modified with at least one divalent or polyvalent metal salt of an organic or inorganic oxyacid such as calcium sulfate, aluminum sulfate, zinc sulfate, zinc phosphate and the like. Mixtures of divalent or polyvalent metal salts of oxyacids, e.g., aluminum sulfate and zinc phosphate, can be used in the process of this invention. The divalent or polyvalent metal salts of organic or inorganic oxyacids are at times referred to hereinafter as "modifiers". These modified catalysts are believed to have complex structures which are probably comprised of a mixture of species, certain of which may not even be catalytically active. Those species which are catalytically active are believed to have structures of the type depicted by the following formula:

$$[R_1-X_1-M_1]_f-Y_1-[M_3-Y_2]_j-[M_2-X_2-R_2]_g \quad (i)$$

wherein:
  $R_1$ and $R_2$ are independently hydrogen or an organic residue of an organic compound having at least one active hydrogen;
  $X_1$ and $X_2$ are independently oxygen, sulfur or nitrogen;
  $M_1$, $M_2$ and $M_3$ are independently a divalent or polyvalent metal provided at least one of $M_1$, $M_2$ and $M_3$ is calcium;
  $Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;
  j is an integer having a value of from 0 to about 100; and
  f and g are integers having a value such that the sum f+g is equal to the valence of $Y_1$ when j is a value of 0, and f and g are integers having a value such that the sum f+g is equal to the valence of $Y_1$ plus $[M_3-Y_2]_j$ when j is a value other than 0. It is understood that formula (i) is speculation only. As used herein, divalent shall mean a valence of 2 and polyvalent shall mean a valence of more than 2.

For purposes of this invention including the claims hereinafter, it is understood that formula (i) shall be inclusive of polyvalency requirements for $M_1$, $M_2$ and $M_3$ and that such polyvalency requirements are appropriately satisfied in formula (i). It is also understood that any polyvalency requirements of $M_3$ may be satisfied by $R_1-X_1-$ or $R_2-X_2-$.

Another aspect of the invention provides a method for preparing a modified calcium-containing alkoxylation catalyst, which method comprises (i) reacting or solubilizing, at least in part, calcium metal or a calcium-containing compound, e.g., calcium oxide or calcium hydroxide, by mixing with an activator to form a calcium-containing composition having titratable alkalinity, and (ii) reacting the calcium-containing composition with at least one divalent or polyvalent metal salt of an oxyacid under effective reaction conditions to produce the alkoxylation catalyst. The term "solubilizing" as used herein is intended to mean that the calcium is provided in an active form which is not the case when calcium is in the form of calcium oxide or calcium hydroxide, hence a solubilization is believed to exist; however, the term is not intended to be limiting to the formation of a truly dissolved calcium specie (which may or may not exist).

The solubilization is effected by mixing any of calcium oxide and calcium hydroxide, for example, with an activator having the general formula $Z_a-X-Q-Y-Z'_b$ wherein X and Y are the same or different electronegative (relative to carbon), hetero (i.e., non-carbon) atoms selected from the group consisting of oxygen, nitrogen, sulfur and phosphorous; a and b are the same or different integers satisfying the valency requirements of X and Y; Q is any organic radical which is electropositive or essentially neutral relative to X and/or Y, which does not prevent the solubilization, and which contains at least one carbon atom and preferably has the formula $$\left[ \begin{array}{c} R_4 \\ | \\ -C- \\ | \\ R_5 \end{array} \right]_p$$

wherein $R_4$ and $R_5$ are the same or different and are selected from the group consisting of hydrogen and lower alkyl or alkylene groups of one to four carbon atoms, and p is an integer from 1 to 6, preferably 2 to 4; Z and Z' are the same or different and are either hydrogen or an organic radical which does not interfere with the function of the activator for its intended purpose, i.e., its solubilizing and/or stabilizing function, thereby forming a calcium-containing composition which is then reacted with the divalent or polyvalent metal salt of an oxyacid to produce a catalyst which is catalytically active in the alkoxylation of compounds having active hydrogens, especially alcohols.

Solubilization of calcium oxide or calcium hydroxide results in the production of an alkaline slurry, which alkalinity can be detected and measured by titration and which is referred to herein as "titratable alkalinity".

The modified calcium-containing catalyst composition can be directly contacted with alkylene oxides to form alkoxylates of the activator itself, if having an active hydrogen, to produce alkoxylates. If the activator does not have an active hydrogen, excess activator should preferably be removed prior to alkoxylation.

According to further embodiments of this aspect of the invention, an exchange reaction is carried out either prior to or after the reaction of the calcium-containing composition with the divalent or polyvalent metal salt of an oxyacid under conditions at which an exchange reaction will occur, with at least one organic compound having an active hydrogen, e.g., an alcohol, having a higher boiling point (and usually a longer carbon chain length) than said activator to form the corresponding, catalytically active higher boiling derivative. This latter catalytic species can then be directly contacted with alkylene oxide to form alkoxylates of the higher boiling material.

The alkoxylation processes of this invention involve the condensation reaction of an alkylene oxide and at least one organic compound having at least one active hydrogen in the presence of a catalytically effective amount of a modified calcium-containing catalyst as described above. The modifier is employed in an amount of about 0.2 to 0.9, e.g., 0.35 to 0.85, often, about 0.45 to 0.75, times that required to give a normal equivalence of metal to anion, which is sufficient to narrow the distribution of the alkoxylation product mixture and provide at least one alkoxylation specie in an amount of at least about 20 weight percent of the mixture. The modified calcium-containing catalyst is prepared under sufficient agitation to ensure a relatively uniform product. The preferred divalent or polyvalent metal salt of an oxyacid is a metal sulfate. Frequently, the modified calcium-containing catalyst is prepared in a medium having a dielectric constant at 25° C. or its normal boiling point, whichever is less, of at least about 10, preferably, at least about 20, say, about 20 to 50, and frequently about 25 or 30 to 45.

By this invention, alkoxylation product mixtures are provided which have a narrow, but balanced distribution of alkoxylation species. These product mixtures are relatively free from large amounts of substantially higher alkoxylation moieties, i.e, those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species.

The alkoxylation product mixtures prepared by the processes of this invention are characterized as the condensation reaction products of alkylene oxides and organic compounds having at least one active hydrogen in which the mole ratio of reacted alkylene oxide per active hydrogen is at least about 4, say, about 4 to 16 or 24, preferably about 5 to 12. The product mixtures have at least one alkoxylation moiety which constitutes at least about 20, say, about 20 to 30 or 40, and most often about 20 to 30, weight percent of the composition. The alkoxylation mixtures of this invention also have a relatively symmetrical distribution. Hence, the portion of the product mixture having three or more oxyalkylene unit groups (per active hydrogen site of the organic compound) than the peak alkoxylation specie is relatively minor, e.g., often less than about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation specie is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie are present in a weight ratio to the most prevalent alkoxylation specie of about 0.6:1 to 1:1.

The preferred alkoxylation product mixtures of this invention correspond to the formula $$P_n = A \times e - (n - \bar{n})^2 / (2.6 + 0.4\bar{n})$$

wherein n is the number of oxyalkylene groups per reactive hydrogen site for an alkoxylation specie (n must equal at least one) of the composition, $\bar{n}$ is the weight average oxyalkylene number, A is the weight percent of the most prevalent alkoxylation specie in the mixture and $P_n$ is, within plus or minus two percentage points, the weight percent of the alkoxylation specie having n oxyalkylene groups (per active hydrogen site) in the mixture. This distribution relationship generally applies where n is between the amount of $\bar{n}$ minus 4 to the amount of $\bar{n}$ plus 4.

For purposes herein, the average peak alkoxylation specie is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture (including unreacted alcohol), i.e., $\bar{n}$ equals the sum of $(n)(P_n)$ for all the species present divided by 100.

Preferred alkoxylation product mixtures of this invention include poly(oxyethylene)glycols, i.e., CARBOWAX ®, and fatty alcohol ethoxylates, i.e., TERGITOL ®. CARBOWAX ® is the registered trademark of Union Carbide Corporation for a series of poly(oxyethylene)glycols. Ethylene glycol can be used to make the CARBOWAX ® poly(oxyethylene)glycols or the CARBOWAX ® poly(oxyethylene)glycols can be used to make higher molecular weight CARBOWAX ® poly(oxyethylene)glycols. For example, CARBOWAX ® poly(oxyethylene)glycol 200 can be used to make CARBOWAX ® poly(oxyethylene)glycol 400. Specifically, the CARBOWAX ® poly(oxyethylene)-glycols are liquid and solid polymers of the general formula $H(OCH_2CH_2)_wOH$, where w is greater than or equal to 4. In general, each CARBOWAX ® poly(oxyethylene)glycol is followed by a number which corresponds to its average molecular weight. Generally, the invention process is not preferred for using CARBOWAX ® poly(oxyethylene)glycols having an average molecular weight above about 600 to 800 as starting materials because such CARBOWAX ® poly(oxyethylene)glycols are solids at room temperature (although they are liquid at the reaction temperatures, e.g., 110° C.). Examples of useful CARBOWAX ® poly(oxyethylene)glycols are: CARBOWAX ® poly(oxyethylene)glycol 200, which has an average w value of 4 and a molecular weight range of 190 to 210; CARBOWAX ® poly(oxyethylene)glycol 400, which has an average w value between 8.2 and 9.1 and a molecular weight range of 380 to 420; and CARBOWAX ® poly(oxyethylene)glycol 600, which has an average w value between 12.5 and 13.9 and a molecular weight range of 570 to 630.

TERGITOL ® is the registered trademark of Union Carbide Corporation for a series of ethoxylated nonylphenols, primary and secondary alcohols, i.e., nonionic surfactants, and the sodium salts of the acid sulfate of secondary alcohols of 10 to 20 carbon atoms, i.e., anionic surfactants. Examples of the TERGITOL ® nonionic surfactants include TERGITOL ® S Nonionics which have the general formula $CH_3(CH_2)_xCH(CH_3)-O-(CH_2CH_2O)_yH$ wherein x is a value of 9-11 and y is a value of about greater than 1. Examples of the TERGITOL ® anionic surfactants include TERGITOL ® Anionic 08, which is $C_4H_9CH(C_2H_5)CH_2SO_4-Na$; TERGITOL ® Anionic 4, which is $C_4H_9CH(C_2H_5(SO_4Na)CH_2CH(CH_3)_2$; and TERGITOL ® Anionic 7, which is $(C_2H_5) C_2H_4CH(SO_4Na)C_2H_4CH(C_2H_5)_2$.

DETAILED DESCRIPTION

As indicated above, the modified calcium-containing catalysts of this invention are modified with divalent or polyvalent metal salts of organic or inorganic oxyacids such as calcium sulfate, aluminum sulfate, zinc sulfate, zinc phosphate and the like or mixtures thereof. These modified catalysts are believed to have complex structures which are probably comprised of a mixture of species, certain of which may not even be catalytically active. Those species which are catalytically active are believed to have structures of the type depicted by the following formula:

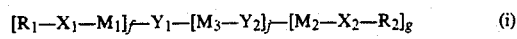

wherein:

$R_1$ and $R_2$ are independently hydrogen or an organic residue of an organic compound having at least one active hydrogen;

$X_1$ and $X_2$ are independently oxygen, sulfur or nitrogen;

$M_1$, $M_2$ and $M_3$ are independently a divalent or polyvalent metal provided at least one of $M_1$, $M_2$ and $M_3$ is calcium;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum $f+g$ is equal to the valence of $Y_1$ when j is a value of 0, and f and g are integers having a value such that the sum $f+g$ is equal to the valence of $Y_1$ plus $[M_3-Y_2]$ j when j is a value other than 0. It is understood that formula (i) is speculation only.

The alkoxylation product mixtures of this invention are enabled by the use of modified calcium-containing catalysts that have been modified by divalent or polyvalent metal salts of strong oxyacids or mixtures thereof sufficient to provide a defined narrow distribution of alkoxylation products. The alkoxylation conditions may otherwise vary while still obtaining a narrower distribution of alkoxylate products.

The modifier of the catalyst is at least one divalent or polyvalent metal salt of an oxyacid and contains at least one, most often at least about 2, oxygen atoms that are conventionally depicted as double bonded to the nucleus atom. Such divalent or polyvalent metal salts include, for example, the sulfates and phosphates of calcium, magnesium, zirconium, zinc and thorium; however, in general the most narrow distributions are obtained using the sulfates.

The types of divalent and polyvalent anions of metal salts of oxyacids suitable for use in this invention, e.g., $Y_1$ and $Y_2$, include by way of example only, sulfates, e.g., $SO_4^{-2}$, phosphates, e.g., $PO_4^{-3}$, maganates, e.g., $MnO_4^{-2}$, titanates, e.g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates, and the like.

Illustrative of metals which may be incorporated into the modifier include beryllium, magnesium, calcium, strontium, barium, scandium, yttrium, lanthanum, titanium, zirconium, hafnium, vanadium, niobium, tantalum, chromium, molybdenum, tungsten, manganese, iron, cobalt, nickel, copper, zinc, cadmium, mercury, boron, aluminum, gallium, indium, thallium, carbon, silicon, germanium, tin, lead, phosphorus, arsenic, antimony, sulfur, selenium, tellurium, cerium, praseodymium, neodymium, promethium, samarium, europium, gadolinium, terbium, dysprosium, holmium, erbium, thulium, ytterbium, lutetium, thorium, protactinium, uranium and plutonium.

Such metals may also be incorporated into the modified calcium-containing catalyst structure by the processes of this invention to provide modified calcium-containing bimetallic or polymetallic catalysts in which the metals incorporated into the catalyst structure can be the same or different. As used herein, bimetallic shall mean 2 metals which can be the same or different and polymetallic shall mean more than 2 metals which can be the same or different.

The amount of modifier employed and the manner in which it is introduced to prepare the catalyst can be determinative of whether the desired narrow distribution with at least one alkoxylation specie being present in an amount of at least about 20 weight percent of the composition, is achieved. While not wishing to be limited to theory, it is believed that active catalysts for producing narrow distributions of alkoxylation products comprise a calcium atom and another metal atom(s)in association with the modifier anion in a manner in which the calcium atom and/or metal atom(s) is activated as illustrated by formula (i) hereinabove. The amount of modifier added is in an amount of about 0.2 to 0.9, say, about 0.45 to 0.75, times that required to give a normal equivalence of metal to anion.

In general, at the time of modification, a precursor composition to the calcium-containing catalyst may be represented by the following formula:

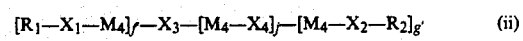

$$[R_1-X_1-M_4]_{f'}-X_3-[M_4-X_4]_j-[M_4-X_2-R_2]_{g'} \quad (ii)$$

wherein $R_1$, $R_2$, $X_1$, $X_2$ and j are as defined hereinabove;

$M_4$ is calcium;

$X_3$ and $X_4$ are independently oxygen, sulfur or nitrogen; and f' and g' are integers having a value such that the sum $f'+g'$ is equal to the valence of $X_3$ when j is a value of 0, and f' and g' are integers having a value such that the sum $f'+g'$ is equal to the valence of $X_3$ plus $[M_4-X_4]_j$ when j is a value other than 0. $R_1$ and $R_2$ independently may also contain double bonded oxygen (the organic compound was a carboxylic acid), heteroatom such as oxygen, sulfur, nitrogen and phosphorous (e.g., the organic compound was a glycol, polyamine, ether of a glycol or the like). Frequently, $R_1$ and $R_2$ may comprise 1 to 20 carbons. It is understood that formula (ii) is speculation only.

For purposes of this invention including the claims hereinafter, it is understood that formula (ii) shall be inclusive of polyvalency requirements for $M_4$ and that such polyvalency requirements are appropriately satisfied in formula (ii). It is also understood that any polyvalency requirements of $M_4$ in $[M_4-X_4]_j$ may be satisfied by $R_1-X_1-$ or $R_2-X_2-$.

The modifier appears to enable the desired catalytically active modified calcium-containing species to form; however, it has been found that depending upon other conditions during the modification, different amounts of modifier will provide the optimum catalyst in terms of selectivity and reaction rate during an alkoxylation process. Accordingly, an aspect of the invention is providing a level of modification sufficient to achieve the narrow distribution of alkoxylate product mixtures.

The medium containing the modified calcium-containing catalyst can also affect whether the resulting modified calcium-containing catalyst enables the desired narrow distribution of alkoxylation products to be formed. If the medium comprises as the predominant component, i.e., solvent, a material that has a low dielectric constant, the modifier can form a separate liquid phase and increased difficulty in obtaining an intimate admixture may be observed. On the other hand, with solvents that are too polar, the organic moiety in association with the calcium atom or metal atom may be displaced with the solvent. Accordingly, undue amounts of water are typically avoided during the modification of the calcium-containing catalyst. Most often, the medium and the organic compound providing the moiety on the calcium atom or metal atom are the same. Particularly convenient media include ethylene glycol, propylene glycol, diethylene glycol, glycerol, butanediols, 1,3-propanediol, and the like. Conveniently, the medium employed, if not intended to be a reactant for producing alkoxylates, should have a sufficiently low boiling point that can readily be removed from the catalyst and organic compound reactant mixture by distillation. Most often, the medium comprises a solvent having at least two heteroatoms such as the activators described herein.

The modifier is preferably added while the calcium-containing precursor composition is being vigorously agitated. In this regard, a slow addition of the modifier to the calcium-containing catalyst is preferred. Generally, less than 10 percent of the modifier to be added is added to the calcium-containing catalyst at any one time. The addition of the modifier can be conducted at a convenient temperature. e.g., about 10° C. to 160° C., say, about 50° C. to 150° C. Preferably, a nitrogen atmosphere is advantageous. It may be advantageous to introduce the modifier in aqueous form.

The calcium-containing catalyst having substituents of the formulae $R_1X_1$— and —$X_2R_2$ may be prepared in any suitable manner. For example, a catalyst precursor can be prepared by reacting calcium metal or a calcium-containing compound such as calcium hydride or acetylide or other suitable source of calcium described below with an organic compound containing an active hydrogen atom of the formula $R_1X_1H$ or $HX_2R_2$. With compounds having higher molecular weights, e.g., 4 or more carbons, it is generally preferred to use a lower molecular weight and more reactive and volatile compound of the formulae $R_1X_1H$ or $HX_2R_2$ (e.g., of 1 to about 3 carbons, especially compounds such as ethanol, ethylamine, ethylene glycol and the like) and then exchange that substituent with the higher molecular weight substituent while removing the lower molecular weight material by volatilization. Alternatively, the calcium-containing catalyst can be prepared from quicklime or slaked lime by the process disclosed hereinafter. The catalyst precursor is then reacted with a divalent or polyvalent metal salt of an oxyacid to produce the modified calcium-containing alkoxylation catalyst.

The compounds having the formulae $R_1X_1H$ and $HX_2R_2$ include those organic compounds having active hydrogens described in connection with the alkoxylation products of this invention, such as alcohols, phenols, carboxylic acids and amines. Most often, the compounds having the formulae $R_1X_1H$ and $HX_2R_2$ are alcohols. When an exchange reaction is to be conducted to provide a higher molecular weight substituent on the calcium atom or other metal atom, it is generally preferred to conduct the modification prior to exchange and use a lower molecular weight material for the replacement substituent to enhance the modification process. Suitable organic compounds having active hydrogens for use in this invention include the products of hydroformylation/hydrogenation reactions.

Illustrative of calcium-containing compounds/compositions for use in this invention include soluble calcium-containing compounds/compositions per se or calcium-containing compounds/compositions which can be converted to a soluble form upon interaction with the alkoxylation process reactants, e.g., activator. Examples of specific calcium-containing compounds/compositions include one or more reaction products of calcium with various alcohols (alcoholates such as calcium alkoxides and phenoxides) as well as oxide, hydroxide, ammoniate, amide, thiolate, carbide, thiophenoxide, nitride, thiocyanate and carboxylate compounds, e.g., acetates, formates, oxalates, citrates, benzoates, laurates and stearates. The preferred calcium-containing compounds are calcium oxide and calcium hydroxide or mixtures thereof, and the preferred calcium-containing compositions are calcium alcoholates.

The preparation of the modified calcium-containing catalyst composition from calcium metal or a calcium-containing compound such as calcium hydride or acetylide or other suitable source of calcium described above is typically conducted at elevated temperatures, e.g., from about 30° C. to 200° C. or more, and in a liquid medium. The organic compound which provides the substitution is normally provided in excess of that required for reaction with the calcium-containing reactant. Hence, the weight ratio of calcium-containing reactant to the organic compound frequently is within the range of about 0.01:100 to 25:100. The reaction may, if desired, be conducted in the presence of an inert liquid solvent. The exchange reaction is also conducted under elevated temperature and, optionally, under reduced pressure to facilitate removal of the more volatile components. Temperatures may range from about 50° C. to 250° C., say, about 80° C. to 200° C. or 250° C., and pressures (absolute) are often in the range of 1 millibar to 5 bars, e.g., about 10 millibars to 2 bars.

It is usually desired that the organic substituent on the modified, calcium-containing catalyst composition correspond to the "starter" component for the alkoxylation process. The starter component is the organic compound having at least one active hydrogen with which the alkylene oxide reacts.

The alkoxylation is conducted using a catalytically-effective amount of the calcium-containing catalyst, e.g., about 0.001 to 10, often about 0.5 to 5, weight percent based on the weight of the starter component. The catalysts substantially retain their activities during the alkoxylation, regardless of the amount of alkylene oxide employed. Thus, the amount of catalyst can be based on the amount of starter provided to the alkoxylation zone and not the degree of alkoxylation to be effected.

Normally, the calcium-containing catalyst and the starter component are admixed and then the alkylene oxide is added at the reaction temperature until the desired amount of alkylene oxide has been added, then the product is neutralized and can be finished, if desired, in any procedure including stripping unreacted starter material from the product mixture, filtration, or further reaction.

The temperature of the alkoxylation is sufficient to provide a suitable rate of reaction and without degradation of the reactants or reaction products. Often, the temperatures range from between about 50° C. and 270° C., e.g. from about 100° C. to 200° C. The pressure may also vary widely, but when low-boiling alkylene oxides such as ethylene oxide and propylene oxide are employed, a pressurized reactor is preferably used.

The alkoxylation reaction medium is preferably agitated to ensure a good dispersal of the reactants and catalyst throughout the reaction medium. Also, the alkylene oxide is usually added at a rate approximating that which it can be reacted.

Neutralization may assist in the recovery of the catalyst from the alkoxylation product mixture. When neutralizing, acids that may tend to form catalyst-containing gel structures or solids that clog filtering apparatus should be avoided. Conveniently, sulfuric acid, phosphoric acid, propionic acid, benzoic acid and the like are used.

The present invention provides a preferred procedure whereby calcium oxide (quicklime) and its hydrated form, calcium hydroxide (slaked lime) (both herein referred to as "lime"), can be effectively used to prepare catalytic species which are active in the alkoxylation of organic compounds having at least one active hydrogen such as alcohols, especially long-chain fatty alcohols, carboxylic acids, amines, polyols and phenols. This is accomplished by the following general procedure.

A catalyst precursor is prepared by contacting lime with an activator under conditions at which the lime and the activator will react or interact to form one or more catalytically active derivatives, hereinafter referred to collectively as "the precursor". The activator may be any compound having the formula $$Z_a-X-Q-Y-Z'_b$$

wherein the various terms are as previously defined. Calcium-containing alkoxylation catalysts incorporating the precursors of this reaction are especially effective in the alkoxylation of alcohols, particularly primary alcohols such as the long-chain fatty alcohols, or mixtures thereof, which are used as starters in the manufacture of nonionic surfactants. However, calcium-containing alkoxylation catalysts incorporating the precursor can also be effectively used in the catalytic reaction of a wide variety of organic compounds containing active hydrogen. If, for example, the activator is ethylene glycol, the precursor can readily be utilized in situ to catalyze the alkoxylation of ethylene glycol itself, thereby producing ethylene glycol-started poly(oxyalkylene)glycols of any desired nominal molecular weight and advantageously having a relatively narrow molecular weight distribution.

If, by way of further example, the activator is the monoethyl ether of ethylene glycol (MEEG) and the precursor is directly alkoxylated with ethylene oxide, the product will be a mixture of ethoxylates of MEEG whose composition will be determined by the molar ratio of ethylene oxide to MEEG.

As used herein, the term "excess activator" means that amount of activator which is not chemically or physically bound to calcium and thus can be removed by simple physical means. The technique employed for this operation is not critical. Vacuum stripping is recommended for its simplicity and efficiency, but evaporation and other known procedures may also be used.

The precursor will be obtained as a finely divided, particulate solid, in slurry form, which can be readily separated from the reaction mixture by filtration, decantation, or similar procedures. The product so obtained is catalytically active in alkoxylation reactions, whether or not modified with a divalent or polyvalent metal salt of an oxyacid.

It is a particularly desirable feature of this invention that the catalyst can be used to provide alkoxylate surfactants having a uniquely narrow molecular weight distribution, low pour point, and low level of unreacted starter component. In this usage, the catalyst is contacted with the starter component, e.g., alcohol, under conditions at which reaction will occur, to perform an alcohol-exchange (which can also be referred to as an alkoxide exchange) reaction. A portion of the starter alcohol thus is present as an alcoholate of calcium, which alcoholate is itself an active species for the alkoxylation reaction. This reaction mixture is then reacted with one or more alkylene oxides, e.g., alkylene oxides such as ethylene oxide, according to known procedures to produce the desired surfactant.

Referring now to the structural formula given above for the activator, X and Y are preferably more than one carbon removed from each other, e.g., in the beta position relative to each other, and are preferably oxygen, as in ethylene glycol, or oxygen and nitrogen, as in monoethanolamine; however, X and Y can also be sulfur or phosphorous. Exemplary of other useful compounds are ethylenediamine, N-methylethanolamine, tetrahydrofurfuryl alcohol, 2-mercaptoethanol, 1,2-propylene glycol, 2-methylthioethanol, 2-ethoxyethanol, diethylene glycol, 1,3-propanediol and 1,4-butanediol.

Z and Z' are the same or different radicals, optionally substituted, and often at least one of Z and Z' is selected from the group consisting of hydrogen, lower linear or branched alkyl of one to four carbon atoms, alkylene from two or about six carbon atoms, phenyl or lower alkyl-substituted phenyl, cycloalkyl of three to about six carbon atoms and alkylene or heteroatom-substituted alkylene rings.

In the activator, Q may comprise a carbon chain of up to six carbons between X and Y. A two-to four-carbon chain is preferred, however, because the activating capacity of X and Y is maximized at such chain lengths. Of these, a two-carbon chain length is especially preferred. In highly preferred embodiments, Q will be a two-carbon chain and the structural formula will be as follows:

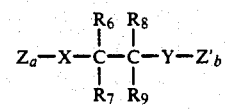

wherein Z, Z', X, Y, a and b are as defined hereinabove and $R_6$, $R_7$, $R_8$, and $R_9$ are preferably hydrogen, but may also be lower alkyl or alkylene groups of one to four carbon atoms, optionally substituted, or such other radicals as do not interfere with the usefulness of the activator for its intended purpose.

Also, Q may be cyclic, preferably cycloalkyl of six or fewer carbons, optionally substituted, as can be represented by the formula:

Compounds coming within this description would include 4-methoxycyclohexane 1,2-diol; 2-aminocyclopentanol; and 2-methoxycyclopentanol.

Similarly, either X or Y or both of them could be part of a ring structure with a carbon atom adjacent to either of them, as illustrated by the formula:

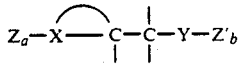

Some compounds illustrating such configurations would include tetrahydrofurfuryl alcohol; furfuryl alcohol; 2-hydroxyethyl aziridine; 1-(N-methyl-2-pyrrolidinyl) ethanol; and 2-aminomethylpyrrolidine.

Moreover, X and Y can themselves be part of the same ring structure, including Q, according to the formula:

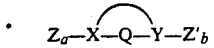

Exemplary of such compounds would be piperazine; 4-hydroxymethyl-2,2-dimethyl-1,3 dioxolane; 2,6-dimethylmorpholine; and cyclohexanone ethylene ketal.

Numerous other ring structures, whether saturated or unsaturated, substituted or unsubstituted, are also possible and are intended to be within the scope of the present invention.

The only perceived limitation on Q and on the overall structure of the formula is that the activator must be capable of solubilizing, at least in part, CaO and/or Ca(OH)$_2$. The solubilization of the normally insoluble CaO and Ca(OH)$_2$ is considered to be the threshold step which permits these heretofore inoperable materials to be successfully utilized. Without intending to be bound to any particular theory, this solubilization is believed to be accomplished through the electron-withdrawing effects of heteroatoms X and Y in relation to adjacent carbon atoms, thereby increasing the acidity of the activator molecule and also helping it to participate in the formation of complexes with calcium, such as exemplified by the structure:

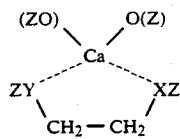

Thus, any structure represented by the formula $Z_a-X-Q-Y-Z'_b$ is satisfactory, provided only that it does not eliminate or neutralize the electronegativity of the heteroatoms and thus prevent the activator from performing its intended purpose of solubilizing, at least in part, the CaO and/or Ca(OH)$_2$. In the method for preparing the modified calcium-containing bimetallic or polymetallic catalysts of this invention, it is believed that the activator may provide a stabilizing effect e.g., thermal stability at high temperatures, for certain intermediate catalytic species prepared in said method, thereby permitting formation of the desired final catalytically active species.

As lime is solubilized, the alkalinity of the medium increases; thus, the building of alkalinity can be used as a screening technique to identify potentially useful activators. In this test, one should look for approximately one or more grams of alkalinity, calculated as CaO, based on 5 grams of calcium (calculated as CaO) charged, as determined by titration with 0.01N HCl in ethanol (alcoholic HCl), as will be described more fully below. It should be noted, however, that amines interfere with this test, thus, it cannot be dependably used with amine-containing activator candidates.

In the solubilizing step of the process of this invention, as has been mentioned above, CaO and/or Ca(OH)$_2$ are mixed with the activator to form one or more precursor species. The purpose of this treatment is to solubilize sufficient lime to be catalytically effective in an alkoxylation reaction; thus, the lime concentration could be either below or above its solubility maximum in the activator, provided only that sufficient lime is solubilized to be catalytically effective. As a general guideline, however, the concentration of lime used in the initial step should typically be in the range of about 1-2%, based on the activator. The lime should normally be present somewhat in excess of its solubility in the activator, but lime concentrations exceeding about 30% would rarely be considered desirable.

The temperature for this procedure is not considered critical, and can range from about 50° C. up to the boiling point of the activator, typically well over 200° C. It is desirable to operate in the range of about 90° to 150° C., preferably about 125° to 150° C., and the system can be put under either vacuum or pressure to maintain any desired temperature while maintaining the activator in the liquid phase. Advantageously, the conditions of temperature and pressure are such that water can be vaporized and removed from the reaction medium. Preferably the catalyst preparation is conducted under a substantially inert atmosphere such as a nitrogen atmosphere.

To perform this step of the process, lime is simply added to the activator in a stirred vessel under sufficient agitation to create a slurry of the lime for a period of time adequate to solubilize at least a portion of the lime. Normally, this will be accomplished within a period of about 1 to 4 hours. The amount of lime which will be solubilized will depend, of course, on the concentration of lime present, the effectiveness of the activator used, and on the temperature, time and agitation employed. Ideally, the quantity of lime desired for the subsequent alkoxylation reaction is solubilized. The source of the lime for this step includes any commercially-available grade of quicklime or slaked lime, since the impurities typically contained in such lime are not believed to significantly adversely affect the catalyst formed by the procedures of this invention.

The resulting lime/activator precursor is then reacted with at least one divalent or polyvalent metal salt of an oxyacid to produce a catalyst for alkoxylation reactions and enhance the narrowness of the alkoxylation product. This would be the case where, for example, ethylene oxide is to be added to the material used as the activator, e.g., ethylene glycol, to produce poly(oxyethylene)glycols of any desired molecular weight.

If the catalyst is to be used to produce a surfactant or other alkoxylation product using a different starter, an exchange can be performed as described above. For example, in producing a surfactant, the catalyst of formula (i) hereinabove can be added to a stirred vessel containing a surfactant range alcohol or mixture of such alcohols, typically C$_{12}$-C$_{14}$ alcohols. The concentration of precursor used can vary over a very broad range, but ideally would be approximately that desired for the subsequent alkoxylation reaction. The temperature during the exchange reaction may be any temperature at which the reaction will occur, but, preferably, will be in the range of about 100°–250° C., and pressure may be adjusted to achieve these temperatures. If the exchange procedure is followed, the activator chosen should have a boiling point of less than about 200° C. to permit it to be readily stripped from the detergent alcohol, most of which boil in the 250° C. range or higher. The resulting alcohol-exchanged product is suitable for use directly as a catalyst in alkoxylation reactions to produce surfactants started with the exchanged alcohol or alcohols.

The catalyst produced by the above-described process is often in the form of a stable slurry of finely divided (e.g., about 5 microns) particles, strongly basic (pH about 11–12), and containing an excess of unmodified calcium-containing species.

The catalyst precursor of formula (ii) hereinabove, including the alcohol-exchanged product thereof, is modified with a divalent or polyvalent metal salt of an oxyacid prior to use as catalyst for alkoxylation to provide a narrow distribution of alkoxylate products. Mixtures of divalent or polyvalent metal salts of oxyacids can be used in the processes of this invention. The modifier can be added at any time during the catalyst preparation but generally is added prior to the addition of a detergent-range alcohol and may be added as a solid or dissolved in an appropriate solvent. While the precise chemical nature of this procedure is not fully understood, the modification does result in a demonstrable improvement to the overall process in that the molecular weight distribution is narrowed. In addition, modified catalysts tend to require little or no induction period in the alkoxylation reaction, and also increase the reaction rate over that of their unmodified counterparts. In contrast, addition of a divalent or polyvalent metal salt of an oxyacid to conventional catalysts, such as potassium hydroxide, slows the alkoxylation rate while producing no beneficial effect on the product distribution.

Advantageous results can be obtained if the catalyst is used in its "crude" form, i.e., without separation from its reaction mixture or purification. Nevertheless, if desired, the catalyst, whether modified or not, can be separated from its reaction mixture, purified, dried and stored. Such may be accomplished in a straightforward manner, as by stripping off the excess activator or other organic material containing active hydrogen, filtering the resulting slurry, reslurrying the wet solids with a solvent (e.g., tetrahydrofuran) and refiltering, and drying, preferably under vacuum. The solids thus obtained will be catalytically active, but, frequently, they are substantially less active than the catalyst in its "crude" form. Reaction rate notwithstanding, however, the desired narrow molecular weight distribution and other benefits can still be obtained.

It is a highly desirable, and quite unexpected, benefit of this aspect of the invention that the overall process embodied in the various procedures described above for making catalysts from lime is remarkably "forgiving" of process variations. Thus, considerable flexibility exists as to the point modifier is added and, within reasonable limits, how much modifier is used. Similarly, the unreacted activator may be removed wholly or partially prior to, e.g., an exchange reaction, if used, or it may be left present during the exchange reaction. Moreover, the catalyst may be re-used indefinitely, used and stored in its "crude" form, or purified and dried, with any loss in reaction rate made up by increasing temperature.

The procedures involved in carrying out the process of this invention are illustrated by the following description directed toward the manufacture of nonionic surfactants.

The manner in which the process of this invention is practiced can be illustrated by the following generalized procedure for preparing a slurry of calcium alkoxylation catalyst intended for use in the manufacture of "peaked" (narrow molecular weight distribution) linear alcohol ethoxylates (nonionic surfactants).

As applied to the specific case of the production of nonionic surfactants, the process of this invention is characterized by a considerable degree of operational latitude. This is particularly true in the preferred version of the process wherein the modified form of the catalyst is produced. From the standpoint of the chemistry which takes place, there are three distinct steps in the preferred preparation of the modified calcium-containing catalysts. Steps 1 and 2 involve the following reactions:

Step 1—Reaction of lime (or mixtures of major quantities of lime with minor quantities of other alkaline earth bases) with a suitable activator to produce a catalyst precursor.

Step 2—Reaction of the catalyst precursor with a detergent range alcohol to effect exchange of the activator-derived organic radicals for detergent-range alcohol-derived organic radicals.

During or following the exchange reactions of step 2 the activator, which preferably is substantially more volatile than the detergent-range alcohol, is removed from the system by distillation. At the conclusion of this operation, the unmodified version of the catalyst is obtained in the form of an activator-free slurry in the detergent-range alcohol.

In the preparation of the intermediate unmodified form of the calcium catalyst, steps 1 and 2, above, may be combined into one operation wherein the lime is reacted with a mixture of activator and detergent-range alcohol. In cases where especially effective activators are being used (e.g., ethylene glycol, 1,2-propylene glycol, ethylene glycol monoethylether, etc.), this alternative procedure of combining the activator with the detergent-range alcohol is frequently preferred because it tends to minimize color build-up in the catalyst slurry. From the standpoint of the final product characteristics, both procedures are equally acceptable. Modified processes wherein the activator is fed into a slurry of the detergent-range alcohol and the calcium base or the detergent-range alcohol is fed into a slurry (or, in some cases, a solution) of the calcium base in the activator are also operationally viable, although their use offers no perceived advantage over the batch-charging version.

The preparation of the modified catalyst involves a third major processing operation which, like that of steps 1 and 2, is a distinct step in terms of the chemistry which takes place.

Step 3—Treatment of the slurry of unmodified catalyst in detergent-range alcohol with a deficiency of at least one divalent or polyvalent metal salt of an oxyacid.

This step provides a highly-active, modified calcium-containing catalyst in the form of a slurry in the detergent-range alcohol. The product slurry is normally subjected to an in vacuo drying operation before it is employed in an ethoxylation reaction to manufacture a nonionic surfactant. The modifier charge can be based either upon the initial lime charge or, more desirably where possible, upon an "active catalyst" value which is obtained by titrating a sample of the lime/activator reaction mixture for alkalinity content using 0.01N alcoholic HCl in the presence of bromothymol blue indicator. A particularly convenient procedure is to follow the course of the lime/activator reaction by titration and to base the modifier charge upon the alkalinity value obtained when a constant level of alkalinity has been reached. An especially convenient and effective procedure, for example, is to add the modifier at a level of about 50% of this "constant" alkalinity value. Monitoring of the lime/activator reaction by titration and ultimately determining the modifier charge based upon this analysis, although frequently a preferred procedure, cannot be used with amino-functional activators because the amine functionality interferes with the alkalinity analysis. In such instances, the preferred procedure is to base the modifier charge on the alkalinity value obtained by titrating the activator-free (stripped) slurry of catalyst in detergent alcohol.

Because of the fact that this process offers such wide operational latitude, there is no single procedure which can be said to represent the general procedure. This consideration notwithstanding, one procedure which will suffice to illustrate the process is as follows:

Lime (as commercially supplied or calcined 6 hours at 600° C.) and 2-ethoxyethanol (available from Union Carbide) are charged to a suitably-sized, agitated vessel equipped with a reflux condenser, thermocouple, 10-tray distillation column, and inert gas purge inlet. The reactants are charged in weight ratios ranging from 60 to 80 parts of 2-ethoxyethanol to one part of lime. The charge is heated under a nitrogen purge for a period of 2 to 6 hours at the reflux temperature (about 135° C.) while refluxing solvent is removed overhead continuously or intermittently at a make rate sufficiently slow such that during the entire reaction period only about 10 to 15% of the original solvent charge is removed overhead. The purpose of this operation is to remove from the system water which was either introduced with the reactants or produced by chemical reaction. During the reflux period, the reaction mixture is sampled at periodic intervals to monitor the buildup of "alkalinity" which is indicative of the formation of catalytically active materials. The analytical method used for this purpose is a titration with 0.01N HCl in 2-ethoxyethanol using bromothymol blue indicator. When similar "alkalinity" levels are obtained from two successive titrations, the lime/activator reaction step is considered to be finished. The usual timed period to reach this point is about 4 hours.

At this point the reaction mixture is diluted with the detergent range alcohol to be ethoxylated; typically the quantity of alcohol added is about 100 grams/gram of lime (calculated as CaO) used in the initial reaction. The resulting mixture is cooled to about 75° C. and treated, under agitation, with sufficient modifier, preferably a metal sulfate, to modify about 60% (on an equivalents basis) of the lime/activator reaction mixture.

The temperature is then increased to permit removal of the activator from the reaction mixture by distillation. Distillation is continued until the kettle temperature reaches about 215° to 225° C. and both the kettle product and the distillate are free of activator as indicated by gas chromatographic (GC) analysis (e.g., less than 1000 ppm by weight and often less than 100 ppm by weight).

The thus-obtained activator-free slurry of catalyst in detergent alcohol can either be used directly as a charge to the ethoxylation reactor or, optionally, diluted with sufficient, dry detergent-range alcohol to afford any desired catalyst concentration in the slurry. A final "alkalinity" value on this slurry may, if desired, be obtained by the same titration procedure described hereinabove.

The above procedure represents but one of many equally viable versions of this process. The examples hereinafter illustrate the use of other versions which are possible through different combinations of the options available in the various process steps.

The catalytic alkoxylation reactions of this invention can be effected, for example, by conventional methods such as (1) batch processes; (2) continuous fixed-bed processes; and (3) continuous fluidized reactor processes. In a batch reactor, the catalyst is kept suspended in the reactant by shaking or stirring. In a fluidized reactor, the catalyst is at a particular original level. As the velocity of the reactant stream is increased, the catalyst bed expands upward to a second level, and at a critical velocity it enters into violent turbulence. The fluidized reactor is particularly useful for removing or supplying the heat necessary to maintain a fixed catalyst temperature. The fluidized reactor can usually be employed only on a rather large scale since good fluidization requires a reactor larger than about 1.5 inches in diameter.

The processes of this invention broadly involve the use of calcium-containing catalysts for the alkoxylation of active-hydrogen compounds, preferably hydroxyl-containing compounds, such as, primary or secondary alcohols, diols or triols. Mixtures of active-hydrogen compounds can be used.

Alkoxylation product mixtures prepared by the processes of this invention comprise alkoxylation species that can be represented by the formula

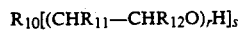

$$R_{10}[(CHR_{11}-CHR_{12}O)_rH]_s$$

wherein $R_{10}$ is an organic residue of an organic compound having at least one active hydrogen, s is an integer of at least 1 up to the number of active hydrogens contained by the organic compound, $R_{11}$ and $R_{12}$ may be the same or different and can be hydrogen and alkyl (including hydroxy- and halo-substituted alkyl) of, for example, 1 to 28 carbons, and r is an integer of at least 1, say, 1 to about 50.

Organic compounds having active hydrogens include alcohols (mono-, di- and polyhydric alcohols), phenols, carboxylic acids (mono-, di- and polyacids), and amines (primary and secondary). Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms. The organic compounds having active hydrogens can be the products of hydroformylation/hydrogenation reactions.

Particularly preferred alcohols are primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenyls of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

The alkylene oxides which provide the oxyalkylene units in the ethoxylated products include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorhydrin and epibromhydrin. The preferred alkylene oxides are ethylene oxide and propylene oxide.

The selection of the organic residue and the oxyalkylene moieties is based on the particular application of the resulting alkoxylation product. Advantageously, narrow distributions can be obtained using a wide variety of compounds having active hydrogens, especially monohydric alcohols, which provide desirable surfactants. Because of the narrow distribution of the alkoxylation product mixture, especially attractive alkoxylation products are surfactants in which certain hydrophilic and lipophilic balances are sought. Hence, the organic compound often comprises a monohydric alcohol of about 8 to 20 carbons and the alkylene oxide comprises ethylene oxide.

While the processes described herein are capable of selectively providing narrow distributions of alkoxylates with the most prevalent having as low as one mole of oxyalkylene per mole of active hydrogen site, a particular advantage exists in the ability to provide a narrow distribution at higher levels of alkoxylation, e.g., wherein the most prevalent specie has at least 4 oxyalkylene units. For some surfactant applications, the most prevalent alkoxylation specie has 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation is narrow, but not so narrow that a range of activity is lost.

Moreover, the relatively symmetrical distribution of alkoxylate species that can be provided by this invention enhances that balance while providing a mixture that exhibits desirable physical properties such as cloud point, freeze point, viscosity, pour point and the like.

For many alkoxylation mixtures of this invention, the species falling within the range of -n plus or minus two comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 20 to about 30 weight percent, e.g., about 22 to 28, weight percent, to enhance the balance of the composition.

Another class of alkoxylation product mixtures are the poly(oxyethylene)glycols. For instance, triethylene glycol and tetraethylene glycol find application in gas dehydration, solvent extraction and in the manufacture of other chemicals and compositions. These glycols can be prepared by the ethoxylation of ethylene glycol and diethylene glycol. Advantageous processes of this invention enable ethoxylate product compositions containing at least about 80, say, about 80 to 95, weight percent of triethylene glycol and tetraethylene glycol.

Among the most commercially important alkoxylation products are those which utilize water or an alcohol (monols, glycols, polyols, etc.) as starter (initiator) and ethylene oxide, propylene oxide, or an ethylene oxide/propylene oxide mixture as the 1,2-alkylene oxide monomer. Such alcohol ethoxylates encompass a myriad of structures, compositions and molecular weights intended for service in a diversity of applications ranging from heavy duty industrial end uses such as solvents and functional fluids to ultra-sophisticated, consumer-oriented end uses such as in pharmaceutical, personal care and household goods. The calcium-containing catalysts of the instant invention find utility in the manufacture of a broad range of alkoxylation products, but are particularly useful in the manufacture of alkoxylates designed for service in sophisticated, consumer-oriented end use areas of application where product quality demands are stringent. Among the many types of alkoxylates which are used in such applications, two of the most prominent are the poly(oxyethylene)glycols and the fatty alcohol under such tradenames as CARBOWAX®, POLYGLYCOL E®, PLURACOL E®, etc., are manufactured by ethoxylation of ethylene glycol or one of its homologues; they are produced over a molecular weight range of about 200 to about 8,000. The fatty alcohol ethoxylates, known under such nonionic surfactant tradenames as NEODOL®, ALFONIC®, TERGITOL®, etc., are manufactured by ethoxylation of linear or branched $C_{10}$—$C_{16}$ saturated alcohols; they are produced over a molecular weight range of about 300 to about 800. It is in the production of these and other performance type, premium quality ethoxylates that the calcium-containing catalysts of the instant invention offer maximum advantages relative to the usual homogeneous ethoxylation catalysts (NaOH, KOH, etc.).

The processes of this invention provide a number of advantages other than selectively providing narrow distributions of alkoxylates. For example, the use of divalent or polyvalent metal salts of oxyacids as modifiers provides safety advantages including handling, storage, etc. The use of divalent or polyvalent metal salts of oxyacids as modifiers also provides processing advantages, e.g., minimum corrosion of reaction equipment and filtration aids (removal of alkoxylation catalyst from final product).

This invention is further illustrated by the following examples.

Examples 1-7 and Comparative Examples A and B

The general procedure described hereinabove was used to produce modified calcium-containing catalysts. Into a 1-liter reaction vessel equipped with a reflux condenser, thermocouple, mechanical stirrer and nitrogen purge inlet was added ethylene glycol and calcium hydroxide (lime) in the amounts specified in Table A below. The resulting mixture was heated to reflux (ca. 105° C.) under reduced pressure (15 millimeters) for a period of 4-5 hours under constant nitrogen purge, during which time a total of about 45 grams of distillate was removed overhead and analyzed for water. After the heating period, the mixture was cooled to a temperature of 60° C. and a metal sulfate specified in Table A followed by Alfol ® 1214, a mixture of $C_{12}$—$C_{14}$ linear, fatty alcohols (approximately 55/45 weight ratio) commercially available from Vista Chemical Company, Houston, Tex., were added to the reaction mixture in the amounts specified in Table A. The mixture was then heated and ethylene glycol (and residual water) was removed overhead (180 millimeters). When the kettle temperature reached 220° C. (the head temperature was 208° C.), the heat was removed and the contents allowed to cool to ambient temperature. The resulting slurry was then transferred to a glass bottle under nitrogen blanket and capped until use. A quantity of each catalyst in this form was used to make a batch preparation of a nonionic surfactant as described in Examples 8-14 hereinafter.

TABLE A

| Preparation of Modified Calcium-Containing Catalysts | | | | |
|---|---|---|---|---|
| Example No. | Ethylene Glycol (Grams) | Calcium Hydroxide (Grams) | Modifier | Modifier (Grams) |
| 1 | 310 | 5.0 | *$Zr(SO_4)_x$ | 14.60 |
| 2 | 310 | 5.0 | $Th(SO_4)_2$ | 26.20 |
| 3 | 310 | 5.0 | $MgSO_4$ | 5.36 |
| 4 | 310 | 5.0 | $ZnSO_4$ | 12.83 |
| 5 | 310 | 5.0 | $ZnSO_4$ | 6.42 |
| 6 | 310 | 5.0 | $ZnSO_4$ | 8.55 |
| 7 | 310 | 5.0 | $CaSO_4$ | 12.15 |
| A | 310 | 5.0 | $Li_2SO_4$ | 5.71 |
| B | 310 | 5.0 | $KHSO_4$ | 6.05 |

*Commerically available from Magnesium Elektron Inc., Flemington, New Jersey, as zirconium basic sulfate (ZBS) having a nominal $SO_4:ZrO_2$ molar ratio of 0.6:1.

Examples 8-14 and Comparative Examples C and D

The general procedure described hereinabove was used to produce nonionic surfactants. The reactor for these preparations was a 2-gallon stirred autoclave equipped with an automatic ethylene oxide feed system wherein a motor valve controlled the feed of ethylene oxide to maintain about 60 psig pressure. Into the 2-gallon stirred autoclave was added Alfol ® 1214, ethylene oxide and a catalyst slurry (moles of starting calcium exclusive of any metal in added modifier) specified in Table B below in the amounts specified in Table B. The reactions were conducted under a nitrogen atmosphere (20 psig) at a temperature of 140° C. The ethylene oxide feed time and maximum reaction rate are also specified in Table B. The molecular weight distribution of the nonionic surfactant products was determined by gas chromatographic analysis (area %) and the results are given in Table B.

TABLE B

| | Preparation of Nonionic Surfactants | | | | | | | | |
|---|---|---|---|---|---|---|---|---|---|
| Example | 8 | 9 | 10 | 11 | 12 | 13 | 14 | C | D |
| Ethoxylation Process | | | | | | | | | |
| Alfol ® 1214 (grams) | 520 | 520 | 520 | 520 | 520 | 520 | 520 | 520 | 520 |
| Ethylene oxide (grams) | 760 | 762 | 758 | 803 | 762 | 764 | 766 | 749 | 789 |
| Catalyst prepared in Example No. | 1 | 2 | 3 | 4 | 5 | 6 | 7 | A | B |
| Catalyst (moles of calcium) | 0.068 | 0.068 | 0.068 | 0.068 | 0.068 | 0.068 | 0.068 | 0.068 | 0.068 |
| Ethylene oxide feed time (minutes) | 26 | 72 | 435 | 145 | 120 | 60 | 118 | 265 | 440 |
| Maximum reaction rate (grams/minute) | 43 | 72 | 1.9 | 9.2 | 7.8 | 14.7 | 8.0 | 3.3 | 1.5 |
| Product Molecular Weight Distribution | | | | | | | | | |
| $E_0$ | 1.65 | 2.65 | 1.56 | 1.82 | 1.28 | 1.24 | 1.29 | 5.01 | 8.78 |
| $E_1$ | 0.94 | 1.18 | 0.85 | 0.83 | 0.61 | 0.66 | 0.53 | 2.44 | 5.03 |
| $E_2$ | 1.12 | 1.63 | 1.50 | 1.33 | 0.97 | 0.86 | 0.78 | 3.69 | 7.37 |
| $E_3$ | 2.62 | 3.44 | 3.52 | 2.97 | 2.23 | 1.61 | 1.83 | 5.83 | 10.96 |
| $E_4$ | 6.32 | 7.47 | 8.17 | 7.22 | 5.64 | 3.96 | 4.61 | 8.61 | 13.75 |
| $E_5$ | 13.48 | 14.23 | 15.14 | 15.04 | 12.34 | 9.49 | 10.52 | 11.45 | 14.68 |
| $E_6$ | 20.86 | 19.97 | 20.41 | 21.32 | 19.71 | 16.93 | 17.73 | 13.45 | 13.19 |
| $E_7$ | 22.17 | 20.23 | 20.02 | 20.86 | 21.86 | 21.51 | 21.12 | 13.92 | 9.98 |
| $E_8$ | 16.69 | 15.19 | 14.77 | 14.87 | 17.56 | 19.87 | 18.43 | 12.74 | 6.48 |
| $E_9$ | 9.30 | 8.84 | 8.69 | 8.38 | 10.84 | 13.39 | 12.42 | 10.57 | 3.53 |
| $E_{10}$ | 3.89 | 4.06 | 4.17 | 4.02 | 5.39 | 6.79 | 6.67 | 7.70 | 1.68 |
| $E_{11}$ | 0.86 | 1.04 | 1.16 | 1.32 | 1.53 | 2.91 | 2.81 | 4.00 | 1.36 |
| $E_{12}$ | — | — | — | — | — | 0.72 | 1.02 | 0.50 | — |

The results from Table B demonstrate the effectiveness of the calcium-containing catalysts of this invention which are modified with a divalent or polyvalent metal salt of an oxyacid. As illustrated by Examples 8-14, nonionic surfactants were prepared having a narrow distribution of alkoxylation species and at least one alkoxylation specie constituting at least about 20 weight percent of the product mixture.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

I claim:

1. A method for providing an alkoxylation catalyst comprising:
   (a) reacting or solubilizing, at least partially, calcium metal or a calcium-containing compound, by mixing with an activator having the formula $$Z_a\text{—}X\text{—}Q\text{—}Y\text{—}Z'_b$$

wherein X and Y are the same or different electronegative, heteroatoms selected from the group consisting of oxygen, nitrogen, sulfur and phosphorus; a and b are the same or different integers satisfying the valency requirements of X and Y; Q is an organic radical which is electropositive or essentially neutral relative as to X and/or Y; Z and Z' are the same or different and are either hydrogen or an organic radical which does not prevent said reacting or solubilizing, thereby forming a calcium-containing composition which has titratable alkalinity; and
   (b) reacting the calcium-containing composition with at least one divalent or polyvalent metal salt of an oxyacid wherein the metal is selected from the group consisting of beryllium, magnesium, strontium, barium, lanthanum, titanium, zirconium, hafnium, niobium, tantalum, molybdenum, tungsten, iron, cobalt, nickel, copper, zinc, boron, gallium, silicon, germanium, tin, phosphorus, antimony, sulfur, selenium, tellurium, cerium and thorium under effective reaction conditions to produce the alkoxylation catalyst.

2. The method of claim 1 wherein the calcium-containing compound is selected from oxides, hydroxides, carboxylates, alcoholates, ammoniates, amides, nitrides, thiocyanates, thiolates, carbides, thiophenoxides and substances to which said compounds are converted in situ in said method.

3. The method of claim 1 wherein the calcium-containing compound is a carboxylate selected from acetates, formates, oxalates, citrates, benzoates, laurates, stearates and substances to which said compounds are converted in situ in said method.

4. The method of claim 1 wherein the calcium-containing compound is calcium oxide, calcium hydroxide or mixtures thereof.

5. The method of claim 1 wherein the calcium-containing composition is a calcium-containing alcoholate.

6. The method of claim 1 wherein the activator has the formula:

$$H_a\text{—}X\text{—}\underset{\underset{R_7}{|}}{\overset{\overset{R_6}{|}}{C}}\text{—}\underset{\underset{R_9}{|}}{\overset{\overset{R_8}{|}}{C}}\text{—}Y\text{—}H_b$$

wherein $R_6$, $R_7$, $R_8$ and $R_9$ are the same or different and are selected from the group consisting of hydrogen and lower alkyl or alkylene groups of one to four carbon atoms.

7. The method of claim 1 wherein the activator is ethylene glycol.

8. The method of claim 1 wherein the activator is 2-ethoxyethanol.

9. The method of claim 1 wherein the divalent or polyvalent metal salt of an oxyacid is a metal sulfate.

10. The method of claim 1 wherein the divalent or polyvalent metal salt of an oxyacid is a metal phosphate.

11. The method of claim 1 wherein the divalent or polyvalent metal salt of an oxyacid is a mixture of a metal sulfate and a metal phosphate.

12. The method of claim 1 wherein the divalent or polyvalent metal salt of an oxyacid is zirconium sulfate.

13. The method of claim 1 wherein the divalent or polyvalent metal salt of an oxyacid is zinc sulfate.

14. The method of claim 1 comprising the additional step of reacting the alkoxylation catalyst with an alcohol under conditions at which an alcohol exchange reaction occurs with the alkoxylation catalyst, thereby producing a corresponding alcohol derivative.

15. The method of claim 14 wherein the alcohol is n-dodecanol.

16. The method of claim 14 wherein the alcohol is a mixture of $C_{12}$—$C_{14}$ alcohols.

17. The method of claim 14 wherein the alcohol is a product of a hydroformylation/hydrogenation reaction.

18. The method of claim 14 comprising the additional step of removing some of all activator which is not bound to calcium.

19. The method of claim 14 wherein about 25 to about 90% of the normal equivalence of the divalent or polyvalent metal salt of an oxyacid to calcium is added during step (b).

20. An alkoxylation catalyst prepared by the method of claim 1.

21. An alkoxylation catalyst prepared by the method of claim 14.

22. An alkoxylation catalyst having the formula:

$$(R_1\text{—}X_1\text{—}M_1)_f\text{—}Y_1\text{—}(M_3\text{—}Y_2)_j\text{—}(M_2\text{—}X_2\text{—}R_2)_g$$

wherein:
$R_1$ and $R_2$ are independently hydrogen or an organic residue of an organic compound having at least one active hydrogen;
$X_1$ and $X_2$ are independently oxygen, sulfur or nitrogen;
$M_1$, $M_2$ and $M_3$ are independently a divalent or polyvalent metal provided at least one of $M_1$, $M_2$ and $M_3$ is calcium and at least one of $M_1$, $M_2$ and $M_3$ is a divalent or polyvalent metal selected from the group consisting of beryllium, magnesium, strontium, barium, lanthanum, titanium, zirconium, hafnium, niobium, tantalum, molybdenum, tungsten, iron, cobalt, nickel, copper, zinc, boron, gallium, silicon, germanium, tin, phosphorus, antimony, sulfur, selenium, tellurium, cerium and thorium;
$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;
j is an integer having a value of from 0 to about 100; and
f and g are integers having a value such that the sum f+g is equal to the valence of $Y_1$ when j has a value of 0, and f and g are integers having a value such that the sum f+g is equal to the valence of $Y_1$ plus $(M_3\text{—}Y_2)_j$ when j has a value other than 0.

* * * * *